United States Patent

Berdyaev et al.

[11] Patent Number: 5,432,053
[45] Date of Patent: Jul. 11, 1995

[54] SOLUTION FOR CONSERVATION OF LIVING ORGANS

[76] Inventors: Sergei J. Berdyaev, ul. Timiryazevskaya, d. 6, kv. 6, 125422 Moscow; Svyatoslav O. Gretsky, ul. Smolnaya, d. 23, korp. 2, kv. 131, 125493 Moscow, both of Russian Federation

[21] Appl. No.: 284,572
[22] PCT Filed: Mar. 23, 1992
[86] PCT No.: PCT/RU92/00056
    § 371 Date: Aug. 26, 1994
    § 102(e) Date: Aug. 26, 1994
[87] PCT Pub. No.: WO93/15604
    PCT Pub. Date: Aug. 19, 1993

[30] Foreign Application Priority Data

Feb. 10, 1992 [RU] Russian Federation ............ 5022600

[51] Int. Cl.$^6$ ............................................. A01N 1/02
[52] U.S. Cl. .................................... 435/1; 435/253.6; 435/283; 435/240.2; 435/240.3
[58] Field of Search ............ 435/1, 253.6, 283, 240.2, 435/240.3

[56] References Cited

U.S. PATENT DOCUMENTS

| 4,798,824 | 1/1989 | Belzer et al. | 435/1 |
|---|---|---|---|
| 4,879,283 | 11/1989 | Belzer et al. | 435/1 |
| 4,956,272 | 9/1990 | Kakimoto et al. | 435/1 |
| 4,965,185 | 10/1990 | Grischenko et al. | 435/1 |
| 5,110,722 | 5/1992 | Brockbank et al. | 435/1 |
| 5,306,711 | 4/1994 | Andrews | 435/1 |
| 5,328,821 | 7/1994 | Fisher | 435/1 |
| 5,370,989 | 12/1994 | Stern et al. | 435/1 |

FOREIGN PATENT DOCUMENTS

| 2581289 | 11/1986 | France . |
|---|---|---|
| 2851289 | 11/1986 | France . |
| 2622396 | 5/1989 | France . |
| 3843958 | 7/1989 | Germany . |
| 3822586 | 1/1990 | Germany . |
| 3822856 | 1/1990 | Germany . |
| 1109110 | 8/1984 | U.S.S.R. . |

*Primary Examiner*—Herbert J. Lilling
*Attorney, Agent, or Firm*—Collard & Roe

[57] ABSTRACT

The invention relates to medicine. The disclosed solution contains components in the following ratio, mM/l:

| Sodium chloride | 100.0–117.0 |
|---|---|
| Potassium gluconate | 12.0–17.0 |
| Calcium gluconate | 1.2–2.0 |
| Magnesium sulphate | 8.0–32.0 |
| Trihydroxymethylaminomethane | 2.0–3.0 |
| Local anesthetic | 0.33–2.66 |
| Phenothiazine derivative | 0.01–0.04 |
| Purine derivative | 1.0–2.0 |
| Polyglucine | the balance |

The solution ensures successful conservation of living organs within up to 48 h.

1 Claim, No Drawings

SOLUTION FOR CONSERVATION OF LIVING ORGANS

FIELD OF ART

The present invention relates to medicine and, more specifically, to a solution for conservation of living organs.

BACKGROUND OF THE INVENTION

Known in the prior art are the methods for conservation of living organs and tissues, used in medicine and involving placing said organs and tissues into special conserving solutions followed by storing them under hypothermic conditions International Meeting on Phosphocreatine in Cardiology and Cardiac Surgery, 1989, 14–15 Apr., Schiapparelli Searle (Pavia) P. Mastroberto, "Analisi degli effetti della creatina-fosfato in aggiunta a soluzione cardioplegica", p. 335–342.

Particular difficulties are encountered in conservation during surgical operations and transplantation of such an intensively functioning organ as the heart which is characterized by intensive metabolic processes and energy consumption during its contractions. If only a few years ago the surgeons were capable of protecting the heart against total ischemia by means of cardioplegia in the course of the ist hour, at present the cooling and chemical cardioplegia suggested by the Royal St. Thomas Institute and Hospital (Great Britain) ensures successful conservation of the heart for as long as 4 h. Plegisol (a commercial preparation) based on the cardioplegic solution worked out by the St. Thomas Hospital and manufactured by the Abbott Laboratories, Chicago, U.S.A., is widely used in clinical practice. Introduction of this preparation has improved cellular protection during lengthy open-heart operations, contributed to further improvement of surgical techniques and extended the period of conservation which is indispensable for heart transplantation (International Meeting on Phosphocreatine in Cardiology and Cardiac Surgery, 1989, 14–15 April. Schiapparelli Searle (Pavial) D. J. Hearse "Protection of the Ischemic Myocardium: Cardioplegia", p. 173–183.

However, the conventionally recognized time of heart conservation (4 h) is insufficient for carrying it over large distances, to any point of the globe, where it has to be transplanted to a recipient. The increased duration of conservation must be combined with improved quality and reliability of protecting the cells against ischemic and reperfusion damage.

DISCLOSURE OF THE INVENTION

The main object of the invention lies in changing the qualitative and quantitative composition of the compound in order to evolve a solution for conservation of living organs featuring a longer period of conservation and survival of cells thus ruling out their ischemic and reperfusion damage.

The object is attained by providing a solution for conservation of organs containing sodium chloride, potassium salt, magnesium salt, calcium salt, pH stabilizer and solvent which contains additionally, according to the invention, a local anesthetic, phenothiazine and purine derivatives, potassium and calcium gluconates as substitutes for calcium salts, magnesium sulphate as a substitute for magnesium salt, trihydroxymethylaminomethane as a pH stabilizer, and polyglucin as a solvent, in the following ratios of components, mM/l:

| | |
|---|---|
| Sodium chloride | 100.0–119.0 |
| Potassium gluconate | 12.0–17.0 |
| Calcium gluconate | 1.0–2.0 |
| Magnesium sulphate | 8.0–32.0 |
| Trihydroxymethylaminomethane | 2.0–3.0 |
| Local anesthetic | 0.33–1.66 |
| Phenothiazine derivative | 0.01–0.04 |
| Purine derivative | 1.0–2.0 |
| Polyglucine | the balance |

The claimed solution extends considerably the conservation time of living organs up to 48 h.

BEST MODE OF CARRYING OUT THE INVENTION

The use of polyglucine for solvent increases radically the osmolarity of the solution (from 320 mOSm/l to 595 mOSm/l up) and prevents violent swelling of mitochondria and intracellular edema. The use of potassium and calcium salts in the form of gluconates and magnesium salt in the form of magnesium sulphate instead of chlorides permits reducing the content of chlorine ions in the solution since the toxic effect of the large number of these ions on the membranes of the excitable cells, e.g. myocardine ones, is well known. The local anesthetic, for example lidocaine, procaine, etc. is added into the solution for stabilization of membranes. The phenothiazine derivative, e.g. ethacysine, is used for fixing the intracellular proteins of the calmoduline type and possesses a clearly pronounced antiarrhythmic and antiischemic effects. The purine derivative, for example inosine, is used to make up for the loss of energy reserves of cells since it can penetrate to miofibrillae, stimulate the synthesis of nucleotides and raise the activity of a number of Krebs cycle enzymes.

The claimed solution contains all the three components which, used in large quantities, can serves as independent cardioplegic agents (ions $K^+$, ions $Mg^{2+}$ and a local anesthetic). However, the quantity of each of said components in the claimed solution is considerably smaller than required for cardioplegy should each of them be used independently (e.g. 30–40 mM/l for potassium and magnesium chlorides; 10 mM/l or more for the local anesthetic, whichever of them is used). Such concentrations of the above-mentioned ions and lidocaine as suggested in the disclosed solution cause a reverse stabilization of excitable membranes of cardiomiocytes and other cells and do not bring about their irreversible damage after prolonged total ischemia and subsequent reperfusion. Smaller concentrations deny the possibility of reaching the expected effect, for example during conservation of living organs and cardioplegia while larger concentrations may lead to an irreversible damage to cell membranes.

The utilization of the claimed solution prolongs successful conservation of living organs, for example up to 48 h.

The claimed solution is a colorless transparent liquid with a pH of 7.3–7.8. It is nontoxic and easily dissolves in water.

This solution is produced by simple mixing of its components.

The disclosed solution was tested in experiments involving conservation of the heart of a donor dog followed by transplanting it to a recipient dog. All in all there were 45 experiments whose results are summarized in the Table.

The claimed solution was also tested in experiments involving conservation of kidneys followed by transplanting them to mongrel white rats.

The better understanding of the present invention it will be elucidated by the following examples of its realization.

Example 1

The claimed solution contained components in the following ratio, mM/l:

| | |
|---|---|
| Sodium chloride | 110.0 |
| Potassium gluconate | 16.0 |
| Magnesium sulphate | 16.0 |
| Calcium gluconate | 1.2 |
| Trihydroxymethylaminomethane | 2.0 |
| Lidocaine | 1.0 |
| Ethacysine | 0.01 |
| Inosine | 1.0 |
| Polyglucine | the balance |

The claimed solution was prepared directly before the operation by simple mixing of the components. Its osmolarity was 595 mOSm/l, and pH was maintained at the level of 7.8. The solution was ozonized for 30 min to 400 mm Hg.

The donor was a 15-kg female mongrel dog. After intravenous injection of sodium pentabarbital in a dose of 25 mg/kg bodyweight, the dog was put under artificial respiration, at a breathing rate of 12 per minute, volume 200 ml. The rib cage was dissected sinistrally and dextrally between the third and fourth ribs by a median incision. The main vessels were extracted, the superior cara vein and aorta were cannulated and ligated. The heart-and-lung preparation was extracted from the organism. The trachea was reintubated and the heart-and-lung preparation was transferred into a flack. The claimed cardioplegic solution was used for washing and the liquid flowing off from the heart was collected in a container. The heart was stopped by the claimed cardioplagic solution in one minute's time. Then the heart was extracted, transferred into a 300-ml container filled with the cardioplagic solution, and placed into a refrigerator for 48 h at 7° C.

On expiration of 48 h the heart was removed from the refrigerator and sutured to the recipient dog in a heterotopic position. The recipient was as 11-kg male mongrel dog. On connecting the veins and arteries, the circulation of blood was slowly started in the transplanted heart which was immediately filled and began contracting. Contractions were soon followed by ventricular fibrillation which was arrested by a defibrillating discharge. Then the arterial pressure and ECG readings were recorded, and a bioptic material was taken for an electromicroscopic examination.

The autopsy of the dog's heart after 48-h conservation and transplantation revealed the following changes. Against the background of a good general conservation there were isnignificant changes of the electrommicroscopic picture of the myocardial tissue in the form of a marble-like edema or a more global one with a moderate spread of mitochondrion cristae or a certain lightening of the mitochondrial matrix, a moderate degree of hyperchromatism or a normal conservation of the nuclear membrane. The changes also included an insignificant edema of myocardial fibers with small myofibrilla divergence foci. After reperfusion of the donor's heart with the recipient's blood the above-described minor changes discovered in the conserved heart vanished completely within 30 minutes. Thus, the myocardial tissue was protected by the solution against total ischemia damage within 48 h and subsequent reperfusion.

Example 2

| Composition of the solution, mM/l: | |
|---|---|
| sodium chloride | 117.0 |
| Potassium gluconate | 17.0 |
| Calcium gluconate | 1.0 |
| Magnesium sulphate | 32.0 |
| Trihydroxymethylaminomethane | 2.5 |
| Lidocaine | 1.66 |
| Ethacysine | 0.02 |
| Inosine | 2.0 |
| Polyglucine | the balance |

The disclosed solution was prepared and administered as in Example 1 but with pH=7.4.

The donor was a 5.4 kg female mongrel dog. General anesthesia: intravenous injection of sodium pentabarbital in a dose of 25 mg/kg bodyweight. The process of the operation was similar to that described in Example 1.

The recipient was a 12-kg female mongrel dog. Transplantation of the donor's heart to the recipient dog was as in Example 1 except that the heart was transplanted into a normotopic position. The heart resumed functioning after 10 minutes of slow perfusion with the recipient's blood. Revification of the heart was accompanied by group atrial and ventricular systoles and episodes of ventricular tachycardia. The recorded parameters of ECG and arterial pressure did not reveal any disturbance in heart functioning, dangerous to life. A bioptic sample was taken for electromicroscopic examination. A necropsy of the myocardial tissue of the heart that was conserved for 25 h and transplanted to the recipient revealed some changes similar to those observed in Example 1 though by far less conspicuous, which vanished completely after 30 minutes perfusion of the donor's heart with the recipient's blood. On the next day after recovering from anesthesia the dog felt normal; there were no changes in organs and systems except for some atrial and ventricular extrasystoles recorded on ECG.

Example 3

| Composition of the solution, mM/l: | |
|---|---|
| Sodium chloride | 100.0 |
| Potassium gluconate | 12.0 |
| Calcium gluconate | 2.0 |
| Magnesium sulphate | 8.0 |
| Trihydroxymethylaminomethane | 3.0 |
| Lidocaine | 0.33 |
| Ethacysine | 0.04 |
| Inosine | 1.5 |
| Polyglucine | the balance |

The solution was prepared as in Example 1 though with pH=7.3.

The donor was a 260-g nondescript white male rat. General ether anesthesia. Proximal laparotomy was made on the white line and the intestine was shifted dextrally to expose the surgery field. The kidney artery and the entire kidney vein were carefully exposed. The ureter was also exposed and microsurgical forceps were applied to the kidney artery and vein intersecting underneath. The donor's kidney was extracted from the operation wound and the kidney artery was cannulated. The kidney was washed with the disclosed solution by introducing the latter into the kidney artery at the rate of 1 ml/min until a colorless fluid emerged from the kidney vein, then the kidney was transferred into a chamber filled with the claimed solution. The chamber was placed into a refrigerator and stored for 26 h at 6° C.

The recipient was a 260-g white mongrel male rat. Its kidney was removed as described above and the intenstine was shifted aside to expose the surgery field for transplantation of the donor's kidney. The kidney vessels and the ureter were carefully extracted. Microforceps were applied to the kidney artery and vein and to the ureter intersecting underneath. The second kidney was extracted and removed from the surgery field. The conserved kidney was carried from the refrigerator into the operative field, localizing the kidney artery and vein and the ureter. Then anastomosis was applied between the donor's and recipient's kidney arteries by individual interrupted sutures, using eight 10.0 ligatures. Then anastomosis of the kidney vein was formed by a continuous suture. The forceps were removed and blood circulation was restored in the transplanted organ. The kidney filled evenly with a slight stenosis of the kidney vein wall. Anastomosis was straightened out by puncturing the inferior cava vein with the needle. Three sutures were applied to the ureter. Execution of the anastomosis was slowed down by active dropwise outflow of urine. The wound was sutured up layerwise. On the next day, after recovery from anesthesia the condition of the rat with the transplanted kidney conserved for 26 h was normal. So were the physiological functions, and no disorders were observed in other organs and systems. A blood sample for analysis was taken from the tail vein. Dynamics of kidney weight were checked; the content of adenosinetriphosphate diminished by 15% less than in the control test with the kidney conserved by the cardioplegic solution used at the St. Thomas Hospital.

Industrial Applicability

The present invention can be utilized in medicine, particularly in transplantation of human patient's organs.

TABLE

Dynamics of Physiological Quotients in Animals after Transplantation of the Donor's Heart (conservation time 24 h)

| No. | Physiological quotient | Postoperative period, h | | | |
|---|---|---|---|---|---|
| | | 0 (immediately after transplantation) | 4 | 24 | 48 |
| 1. | Behavior quotients: | | | | |
| 1.1. | Orientation reflexes | none | changed | normal | normal |
| 1.2. | Defense reflexes | none | changed | normal | normal |
| 1.3. | Conditioned reflexes | none | changed | normal | normal |
| 2. | Condition of organs and systems: | | | | |
| 2.1. | Motor activity | none | changed | changed | normal |
| 2.2. | Uresis | changed | changed | normal | normal |
| 2.3. | Digestion | changed | changed | changed | normal |
| 3. | Body temperature | changed | changed | changed | normal |
| 4. | Respiration rate | changed | changed | changed | normal |
| 5. | Respiration depth | changed | changed | changed | normal |
| 6. | Arterial pressure | changed | changed | normal | normal |
| 7. | Heart rate | changed | changed | changed | normal |
| 8. | Pulse | changed | changed | changed | normal |
| 9. | Heart rhythm: | | | | |
| 9.1. | Atrial extraystoles | * | * | * | * |
| 9.2. | Atrial flutter and fibrillations | * | * | * | none |
| 9.3. | Ventricular extraystoles | * | * | * | * |
| 9.4. | Sinus bradycardia | * | * | none | none |
| 9.5. | Sinus tachycardia | ** | * | * | none |
| 9.6. | Supraventricular tachycardia | * | * | * | none |
| 9.7. | Ventricular tachycardia | * | none | none | none |
| 9.8. | Ventricular fibrillation | * | none | none | none |
| 9.9. | Blocks: | | | | |
| 9.10. | Sinusal | * | * | none | none |
| 9.11. | Atrioventricular of various degrees | * | * | none | none |
| 9.12. | His bundle-branch block | * | none | none | none |
| 10. | ECG parameters: | | | | |
| 10.1. | Waves (duration and amplitude): | | | | |
| 10.2. | P | changed | normal | normal | normal |
| 10.3. | Q | changed | normal | normal | normal |
| 10.4. | R | changed | normal | normal | normal |
| 10.5. | S | changed | normal | normal | normal |
| 10.6. | T | changed | changed | changed | normal |
| 10.7. | Intervals: | | | | |
| 10.8. | PQ | changed | normal | normal | normal |
| 10.9. | QRS | changed | normal | normal | normal |

TABLE-continued

Dynamics of Physiological Quotients in Animals after Transplantation of the Donor's Heart (conservation time 24 h)

| No. | Physiological quotient | Postoperative period, h | | | |
| --- | --- | --- | --- | --- | --- |
| | | 0 (immediately after transp- lantation) | 4 | 24 | 48 |
| 10.10. | QT | changed | normal | normal | normal |
| 10.11. | Fragment ST | changed | changed | changed | normal |
| 11.1. | Physiological activity of analyzers: | | | | |
| 11.2. | Visual | changed | normal | normal | normal |
| 11.3. | Acoustic | changed | normal | normal | normal |
| 11.4. | Tactile | changed | normal | normal | normal |
| 11.5. | Vestibular | changed | changed | normal | normal |
| 11.6. | Gustatory | changed | changed | normal | normal |

Symbols:
*data unreliable (p 0.05)
**data reliable (p 0.05)

We claim:

1. A solution for conservation of living organs containing sodium chloride, salts of potassium, magnesium and calcium, a pH stabilizer and a solvent CHARACTERIZED in that it contains additionally a local anesthetic, phenothiazine and purine derivatives, potassium and calcium gluconates as a substitute for potassium and calcium salts, magnesium sulphate as a substitute for the magnesium salt, trihydroxymethylaminomethane as a pH stabilizer, and polyglucine as a solvent in the following ratios of components, mM/l:

| | |
| --- | --- |
| Sodium chloride | 100.0–117.0 |
| Potassium gluconate | 12.0–17.0 |
| Calcium gluconate | 1.2–2.0 |
| Magnesium sulphate | 8.0–32.0 |
| Trihydroxymethylaminomethane | 2.0–3.0 |
| Local anesthetic | 0.33–2.66 |
| Phenothiazine derivative | 0.01–0.04 |
| Purine derivative | 1.0–2.0 |
| Polyglucine | the balance |

* * * * *